United States Patent [19]
Albin

[11] Patent Number: 5,405,313
[45] Date of Patent: Apr. 11, 1995

[54] ADJUSTABLE BACK SUPPORT

[76] Inventor: J. Thomas Albin, 1702 Albin Pond Rd., Greencastle, Ind. 46135

[21] Appl. No.: 81,968

[22] Filed: Jun. 24, 1993

[51] Int. Cl.⁶ .............................................. A61H 1/02
[52] U.S. Cl. .................... 602/19; 602/20; 602/5
[58] Field of Search ........... 602/20, 19, 5; 128/870, 128/874, DIG. 19; 297/411.1, 411.21, 411.2, 411.35, 411.36; 135/68, 71; 2/44, 45

[56] References Cited

U.S. PATENT DOCUMENTS

| | | | |
|---|---|---|---|
| 129,202 | 7/1872 | Zachos | 602/19 |
| 170,655 | 12/1875 | Allen | 128/78 |
| 492,903 | 3/1893 | Gerlitz | 128/78 |
| 970,781 | 9/1910 | Battershall | 128/78 |
| 1,595,739 | 8/1926 | Stewart | 128/78 |
| 1,614,641 | 1/1927 | Anderson | 602/19 X |
| 1,722,205 | 7/1929 | Freund | 602/19 X |
| 2,687,129 | 8/1954 | Talkish | 128/78 |
| 2,859,746 | 3/1956 | Roberson | 128/87 R |
| 2,886,031 | 5/1959 | Robbins | 602/19 |
| 3,029,810 | 4/1962 | Martin | 2/44 X |
| 3,878,841 | 4/1975 | Villanueva | 128/78 |
| 4,644,939 | 2/1987 | Coleman | 602/19 |
| 4,907,575 | 3/1990 | Satterthwaite | 602/19 |
| 5,224,924 | 7/1993 | Urso | 602/20 X |

FOREIGN PATENT DOCUMENTS

| | | | |
|---|---|---|---|
| 55101 | 1/1891 | Germany | 602/19 |
| 37573 | 7/1956 | Poland | 602/19 |

OTHER PUBLICATIONS

Neil Irick, M.D., Albin Brace For Osteoporosis Patients, Jun. 7, 1993, letter, one page, not published. Authentication of efficacy.

*Primary Examiner*—Richard J. Apley
*Assistant Examiner*—Beverly A. Meindl
*Attorney, Agent, or Firm*—H. John Barnett

[57] ABSTRACT

An improved back support comprising a pair of adjustable rigid hip crutches, each extending from one of the hips of the user up under the corresponding armpit to provide evenly distributed back support. Each hip crutch is hingedly attached to the outside surface of a wide belt which encircles the user's waist. As the condition of the back improves, the length of each hip crutch can be increased or decreased as indicated by the individual needs of the user.

4 Claims, 3 Drawing Sheets

ADJUSTABLE BACK SUPPORT

BACKGROUND OF THE INVENTION

1. Field of the Invention

Various conditions of the vertebrae in the human backbone cause deterioration and pain. Such conditions include osteoporosis, osteomalacia, scoliosis, herniated discs, fractures, bone spurs, cancer surgery and any other osteopathic disorder. Some of the disorders cause malfunction of the intervertebral discs and consequent pressure on the spinal nerves.

A conservative treatment for some of the above conditions is to place the patient in a body cast to support the upper body from the relatively stronger pelvis. The body cast may be left in place for up to about six weeks, and is normally not removable for bathing, sleeping and similar activities. In addition, a body cast is usually not adjustable, being custom-made for one patient, and only to suit the patient's condition when the cast is made.

2. Description of Related Art.

U.S. Pat. No. 170,655 describes a back and shoulder brace. This brace appears to have a single shoulder brace M, and the hip supports A,A1 appear to be disposed to the front and back of the wearer, and not under the arms. It does not appear that hip supports A,A1 can be adjusted in length.

U.S. Pat. No. 492,903 shows a flexible brace for curing spinal curvature which relies on lateral forces. The steel supports which extend up from the pelvis belt are disposed at the back, and do not directly support the shoulders.

U.S. Pat. No. 970,781 and 1,595,739 also appear to be intended for treating spinal curvature, and do not have rigid shoulder supports under both arms of the wearer.

U.S. Pat. No. 2,687,129 describes a corrective brace for a scoliosis patient. This device includes a single rigid hip pad, a chest pad, supporting straps carried by the hip and chest pads, a tension strap and aligned connecting bars disposed under one arm and secured to the chest and hip pads. The purpose seems to be to straighten a crooked spine by applying lateral compression.

U. S. Pat. No. 3,029,810 discloses a somewhat similar back brace which has a single adjustable strut which is disposed under one arm of the patient. It also has a pair of arm encircling connected by a shoulder strap. This brace also appears to be intended to give lateral support.

U. S. Pat. No. 3,878,841 shows an adjustable orthotic brace which has a single adjustable support extending from the side of the pelvis up to the armpit of a patient. A cushioned half crutch is connected to the upper end of the adjustable support. A harness holds the crutch in place to support one arm of the patient. A harness is provided to extend across the back of the user, and around the other shoulder to hold the half crutch in place. Each of the above devices provide rigid support only on one side of the user's body.

SUMMARY OF THE INVENTION

This invention is an improvement over the above devices by providing a pair of adjustable, rigid hip crutches, each extending from one of the hips of the user up under the corresponding armpit to provide evenly distributed back support. The bottom end of each hip crutch is hingedly attached to the outside surface of a wide belt which encircles the user's waist. The bottom end of each hip crutch is centered on the lateral portion of the corresponding hip bone. The top end of each hip crutch terminates in a padded arm rest which extends under the corresponding armpit of the user. Together, the rigid hip crutches evenly support the user's back.

A pair of adjustable side straps extend vertically from the back of the belt up over the shoulders of the user, and each side strap connects to the front end of the corresponding arm rest to hold it in place. A horizontal, flexible strap interconnects the vertical side straps across the top of the back to keep the side straps from sliding off the user's shoulders.

Together, the rigid hip crutches evenly support the user's back by supporting the user's upper body directly on the user's hips, thereby relieving strain on the user's thoracic and lumbar vertebrae. As the condition of the back improves, the length of each hip crutch can be increased or decreased as indicated by the individual needs of the user.

DESCRIPTION OF THE PREFERRED EMBODIMENT

Figure 1:
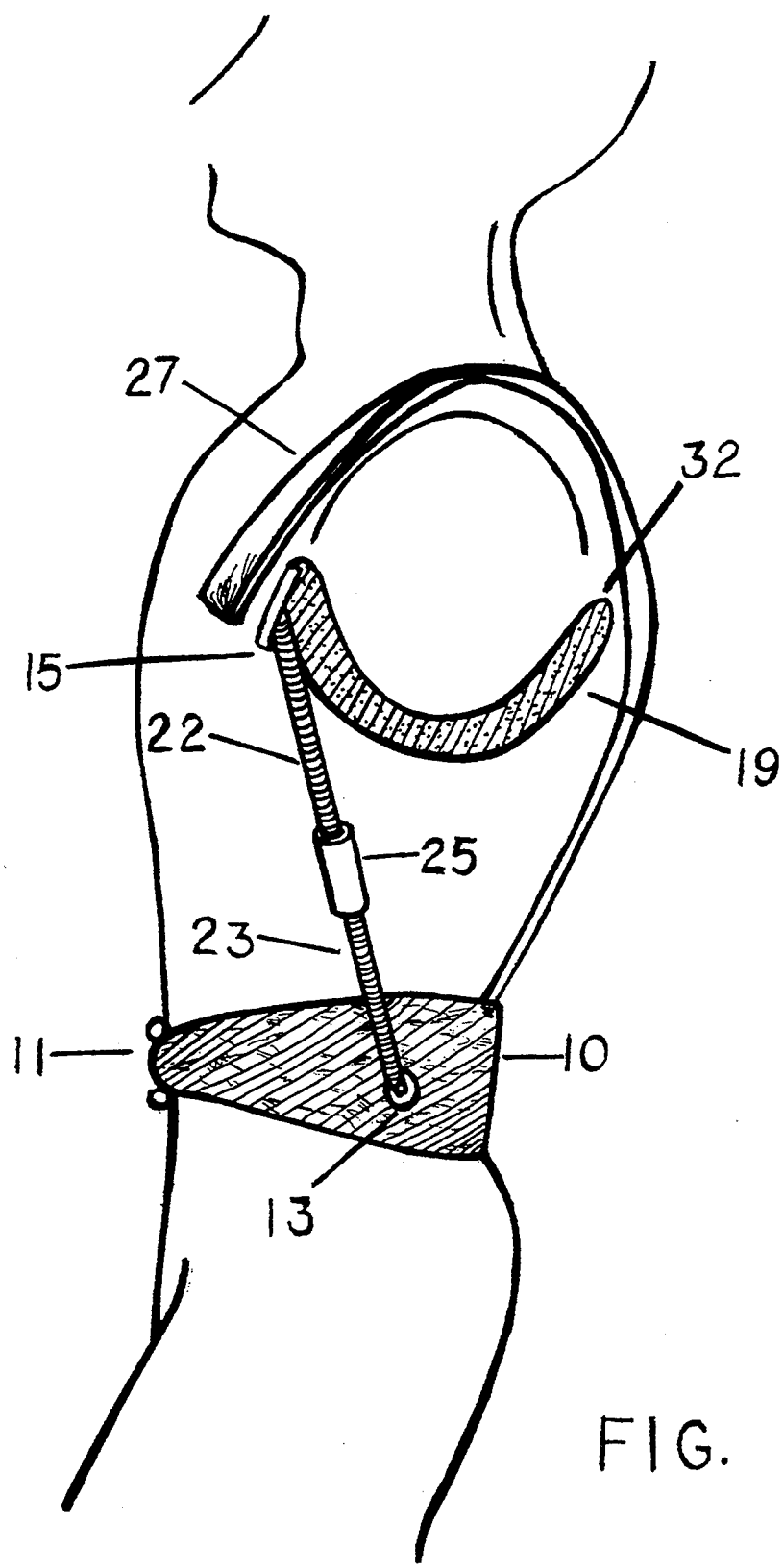
FIG. 1 of the drawings is a schematic side view of the adjustable back support shown in position on a user's body, with some parts broken away, and some parts shown in phantom.
Figure 2:
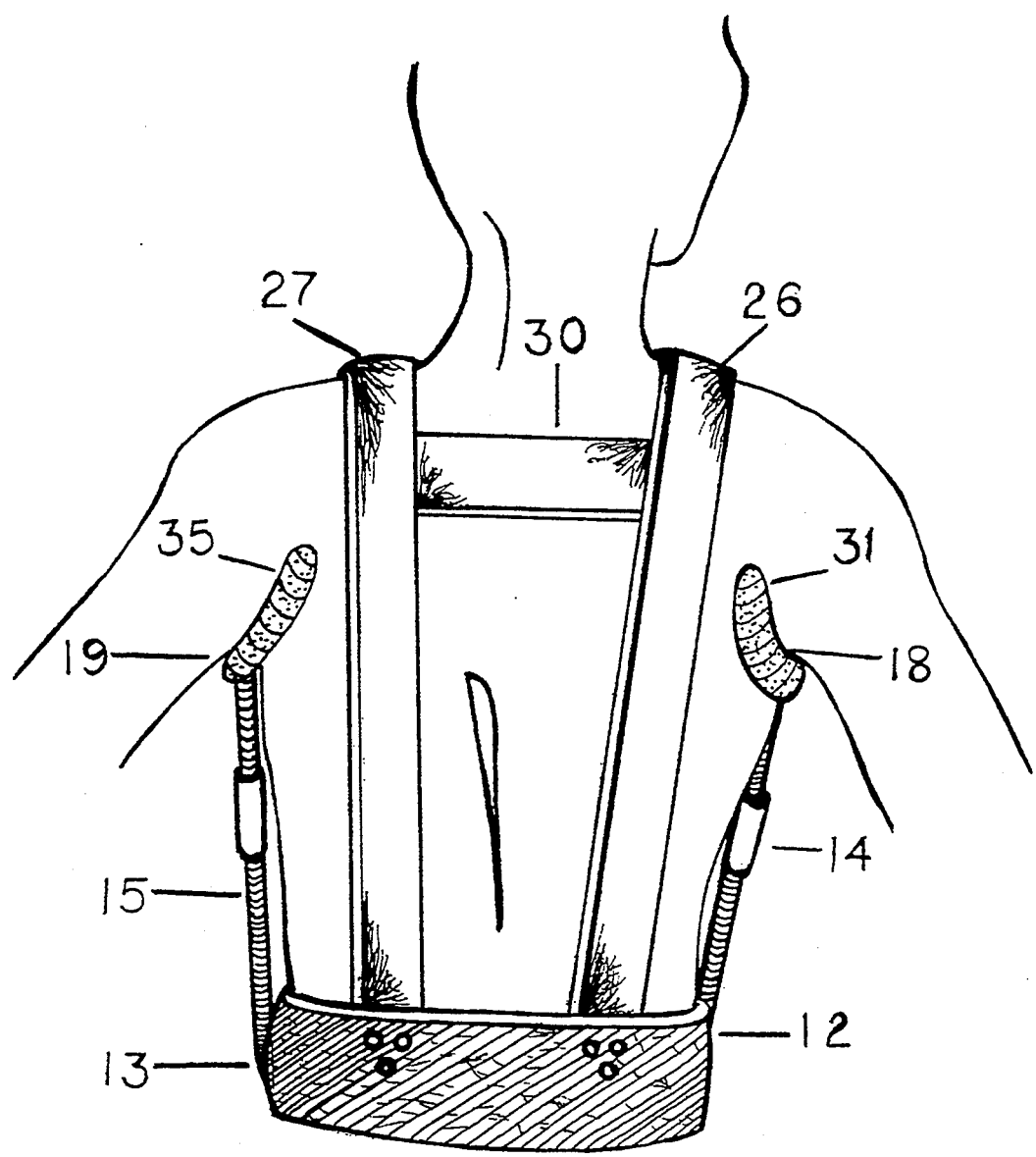
FIG. 2 is a schematic back view of the back support shown in position on a user's body, with some parts broken away and some parts shown in phantom.
Figure 3:
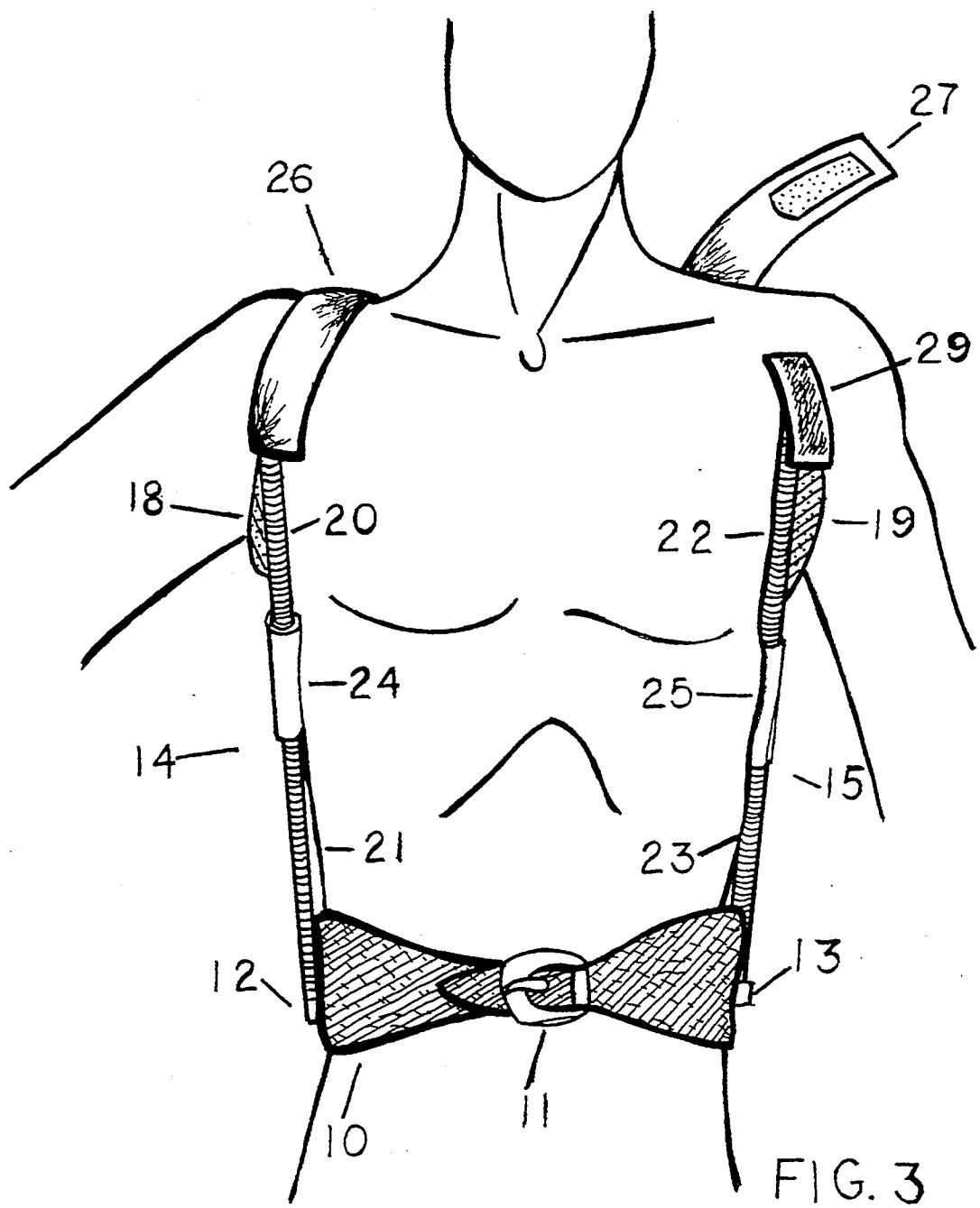
FIG. 3 is a schematic front view of the back support shown in position on a user's body, with some parts broken away.

A hip belt 10, which is about 3.5 inches wide in the back, and about 1.5 inches wide in the front, encircles the user at the waist. The belt 10 is held in close contact with the user's hips by means of a closure 11. A pair of hinged attachments 12 and 13 provide means for securing hip crutches 14 and 15 to the opposite sides of the belt 10.

Each hip crutch 14, 15 includes a rigid support rod which extends upwardly and terminates in an arm rest 18, 19. The support rods each comprise a pair of threaded rods 20 and 21, 22 and 23 which are interconnected by rigid threaded tubular members 24, 25. Turning the rigid tubular members 24, 25 which are threadably coupled on the adjacent threaded rods 20, 21 and the rods 22, 23, respectively, raises or lowers the corresponding arm rest 18 or 19 to snugly fit under the corresponding arm of the user to evenly support the upper body on the hips.

A pair of spaced apart, side straps 26 and 27 are connected to the back of the belt 10, and extend upwardly over the corresponding shoulder to attach to the corresponding arm rest 18 or 19 by means of fasteners 28 and 29. A horizontal strap 30, high on the user's back, interconnects the side straps 26 and 27 to hold them in place. The back ends 31 and 32 of the arm rests 18 and 19 are not attached, and can pivot to fit comfortably under the user's arms.

Assembly of the back support on the user's body is relatively simple. The first arm rest can be first positioned under the corresponding arm with the corresponding side strap already fastened to its front end. The belt 10 is then positioned around the waist, and the second half crutch positioned under the other arm. The second side strap can then be pulled over the shoulder and fastened to the front end of the second arm rest. Securing the belt closure completes the assembly.

Removing the back support is also simple. Both side straps can be unfastened, if desired, to make removal easier. When the belt closure is released, the support can be lowered and easily removed.

The back support can be adjusted periodically as deformed discs heal and start to fill in the spaces between individual vertebrae, or when more weight can be supported by the vertebrae, such as when healing has taken place of a fractured vertebra. The improved back support provides uniform support to both shoulders of the user's body, and can be adjusted to the needs of an individual user.

What is claimed is:

1. An adjustable back support for evenly supporting the upper body to alleviate pack pain and aid in healing disorders of the spinal column, comprising:

a pelvic girdle having a front, a back and two sides, said girdle adapted to fit snugly around the user's waist;

a pair of hip crutches adapted to be vertically disposed on opposite sides of the user's body, each hip crutch extending upwardly at a small forward angle from the pelvic girdle to the corresponding armpit of the user;

each hip crutch including a vertically adjustable rigid support rod having a top and bottom end, the bottom end being connected to the corresponding side of the pelvic girdle, and adapted to extend upwardly at a small forward angle, said support rod being adjustable by the user while wearing the back support;

an arm rest having a front and back end attached at its front end only to the top end of the corresponding support rod, said arm rests being adapted to fit under the user's arms to support the user's upper body directly on the user's hips; and a pair of flexible straps each having first and second ends and intermediate portions, the respective first ends of the straps being attached to the back of the pelvic girdle at points laterally offset to the left and right of the user's spinal column, and the respective second ends being attached to the front end only of the corresponding arm rest to hold the arm rest in position under the user's arm without any strap crossing the user's chest or the middle and lower thoracic region of the user's spine, to thereby relieve strain on the user's thoracic and lumbar vertebrae while permitting greater freedom of motion of the user's upper body.

2. The back brace of claim 1, including a transverse strap connecting the intermediate portions of the flexible straps near their respective upper ends adapted to fit across the scapular region of the user's spine, said transverse strap being adapted to aid in retaining the flexible straps in position over the user's shoulders with minimal contact with the user's spine.

3. The adjustable back support of claim 1, in which the lower ends of the hip crutches are pivotally attached to the pelvic girdle on opposite sides of the user's body to afford greater freedom of movement of the user's upper body.

4. The adjustable back support of claim 1, in which the pelvic girdle comprises a semi-rigid belt having a front, a back and two sides;

pivotal attachment means on said belt on each side thereof for receiving and supporting the bottom end of the corresponding rigid support rod; and closure means disposed on the front of said belt for assembling and removing the adjustable back support from the body of a user.

* * * * *